(12) United States Patent
Lundy et al.

(10) Patent No.: US 11,129,548 B2
(45) Date of Patent: Sep. 28, 2021

(54) METHOD, APPARATUS, AND COMPUTER READABLE MEDIUM FOR GENERATING A SET OF RECOMMENDED ORTHOTIC PRODUCTS

(71) Applicant: Scholl's Wellness Company LLC, Boston, MA (US)

(72) Inventors: Charles Lundy, Summit, NJ (US); Harold Howlett, Parsippany, NJ (US)

(73) Assignee: Scholl's Wellness Company LLC, Parsippany, NJ (US)

( * ) Notice: Subject to any disclaimer, the term of this patent is extended or adjusted under 35 U.S.C. 154(b) by 132 days.

(21) Appl. No.: 16/511,254

(22) Filed: Jul. 15, 2019

(65) Prior Publication Data

US 2019/0336042 A1 Nov. 7, 2019

Related U.S. Application Data

(63) Continuation of application No. 15/303,031, filed as application No. PCT/US2015/025211 on Apr. 9, 2015, now abandoned.

(60) Provisional application No. 61/977,347, filed on Apr. 9, 2014.

(51) Int. Cl.
| | |
|---|---|
| A61B 5/107 | (2006.01) |
| A61B 5/00 | (2006.01) |
| A61B 5/103 | (2006.01) |
| A61B 5/1486 | (2006.01) |

(52) U.S. Cl.
CPC .......... *A61B 5/1074* (2013.01); *A61B 5/0077* (2013.01); *A61B 5/1036* (2013.01); *A61B 5/1072* (2013.01); *A61B 5/1073* (2013.01); *A61B 5/1077* (2013.01); *A61B 5/1079* (2013.01); *A61B 5/1486* (2013.01); *A61B 5/706* (2013.01); *A61B 2576/02* (2013.01)

(58) Field of Classification Search
None
See application file for complete search history.

(56) References Cited

U.S. PATENT DOCUMENTS

| | | | |
|---|---|---|---|
| 5,432,703 A * | 7/1995 | Clynch | A61B 5/0064 700/163 |
| 5,790,256 A * | 8/1998 | Brown | A43D 1/02 33/3 R |
| 9,691,176 B2 * | 6/2017 | Samson | A61B 5/1075 |

(Continued)

*Primary Examiner* — Patrick Fernandes
*Assistant Examiner* — Benjamin S Melhus
(74) *Attorney, Agent, or Firm* — Lowenstein Sandler LLP

(57) ABSTRACT

In an embodiment, the present invention is an apparatus, comprising: a foot mat; a depth sensing camera; an elevated foot platform that reduces or prevents rotational movement of a foot; a processor in communication with the depth sensing camera, the processor further configured to calculate the circumference of a user's leg based on data from the depth sensing camera while the user has one foot on the foot mat and one foot on the elevated foot platform, the processor further configured to select a recommended product for the user's knee or ankle from among a set of pre-manufactured candidate products for knees or ankles based at least in part upon the leg circumference of the user; and an output device to display information received from the processor, the information identifying the recommended product to the user.

11 Claims, 15 Drawing Sheets

(56) References Cited

U.S. PATENT DOCUMENTS

| | | | | |
|---|---|---|---|---|
| 2006/0104503 | A1* | 5/2006 | Huang | A61B 5/0064 |
| | | | | 382/154 |
| 2009/0076772 | A1* | 3/2009 | Hinshaw | A43D 1/025 |
| | | | | 702/167 |
| 2009/0316965 | A1* | 12/2009 | Mailling | A43D 1/025 |
| | | | | 382/128 |
| 2010/0262054 | A1* | 10/2010 | Summit | G06F 30/00 |
| | | | | 602/14 |
| 2014/0063220 | A1* | 3/2014 | Taylor | A61F 5/0106 |
| | | | | 348/77 |
| 2014/0276094 | A1* | 9/2014 | Lidtke | A61B 5/1074 |
| | | | | 600/476 |
| 2014/0300907 | A1* | 10/2014 | Kimmel | A41H 1/02 |
| | | | | 356/625 |
| 2016/0081435 | A1* | 3/2016 | Marks | A43D 1/02 |
| | | | | 382/154 |
| 2016/0093085 | A1* | 3/2016 | Ray | G06T 13/40 |
| | | | | 345/419 |

\* cited by examiner

METHOD, APPARATUS, AND COMPUTER READABLE MEDIUM FOR GENERATING A SET OF RECOMMENDED ORTHOTIC PRODUCTS

BACKGROUND

Conventional orthotic products for upper and lower extremities, such as elbow braces, arm braces, forearm-wrist braces, forearm-wrist-thumb braces, forearm-wrist-hand braces, knee braces, ankle braces, etc., are typically sold from conventional retail displays. Although packaging may provide some guidance, customers may have difficulty understanding which product(s) is/are appropriate in view of the customer's own physical attributes. Further, even if a customer were given an opportunity to try on a product, the customer may not know the most appropriate type of support or size of orthotic product for their particular body configuration e.g., the arch type of the customer's foot, the circumference around their knee or ankle, or activity level. This uncertainty may result in the customer buying multiple products before the customer finally finds a product that meets the customer's needs.

Custom orthotic products may also be sold to provide a customer with the proper level of support. Custom orthotic products may have adjustable support, yet not be of the proper size for a customer's physical attributes and may require significant time to identify the proper sizing. Some custom orthotic products may be made by moldable material. However, this requires time to measure the extremity and then a period of time to make the orthotic product. Because such orthotic products are custom-made, they may be typically more expensive than pre-manufactured orthotics. Also, creating molded orthotic products generally specialized training that measures the physical attributes of the customer and makes or orders the orthotic in accordance to the measured physical characteristics.

The problem of efficiently supporting customers with respect to orthotic products selection was partially addressed by Applicant's prior U.S. Patent directed towards a "Footcare Product Dispensing Kiosk", U.S. Pat. No. 8,117,922, the contents of which are incorporated in their entirety by reference thereto. The Footcare Product Dispensing Kiosk patent addressed the selection of orthotic products for addressing issues related to the bottom of the feet.

SUMMARY OF THE INVENTION

In an embodiment, the present invention is an apparatus, comprising: a foot mat; a depth sensing camera; an elevated foot platform that reduces or prevents rotational movement of a foot; a processor in communication with the depth sensing camera, the processor further configured to calculate the circumference of a user's leg based on data from the depth sensing camera while the user has one foot on the foot mat and one foot on the elevated foot platform, the processor further configured to select a recommended product for the user's knee or ankle from among a set of pre-manufactured candidate products for knees or ankles based at least in part upon the leg circumference of the user; and an output device to display information received from the processor, the information identifying the recommended product to the user.

In an embodiment, the present invention is an apparatus, comprising: a foot mat; a depth sensing camera; an elevated foot platform that reduces or prevents rotational movement of a foot; a processor in communication with the depth sensing camera, the processor further configured to calculate the circumference of a user's leg based on data from the depth sensing camera while the user has one foot on the foot mat and one foot on the elevated foot platform, the processor further configured to select a recommended product for the user's knee or ankle from among a set of pre-manufactured candidate products for knees or ankles based at least in part upon the leg circumference of the user; and an output device to display information received from the processor, the information identifying the recommended product to the user, wherein the elevated foot platform comprises one, two, or three foot wells.

In an embodiment, the present invention is an apparatus, comprising: a foot mat; a depth sensing camera; an elevated foot platform that reduces or prevents rotational movement of a foot; a processor in communication with the depth sensing camera, the processor further configured to calculate the circumference of a user's leg based on data from the depth sensing camera while the user has one foot on the foot mat and one foot on the elevated foot platform, the processor further configured to select a recommended product for the user's knee or ankle from among a set of pre-manufactured candidate products for knees or ankles based at least in part upon the leg circumference of the user; and an output device to display information received from the processor, the information identifying the recommended product to the user, wherein the foot mat is a pressure array foot mat, wherein the processor is in communication with the pressure array foot mat, the processor configured to receive a plurality of pressure measurements from the pressure array foot mat while the user stands thereupon.

In an embodiment, the present invention is an apparatus, comprising: a foot mat; a depth sensing camera; an elevated foot platform that reduces or prevents rotational movement of a foot; a processor in communication with the depth sensing camera, the processor further configured to calculate the circumference of a user's leg based on data from the depth sensing camera while the user has one foot on the foot mat and one foot on the elevated foot platform, the processor further configured to select a recommended product for the user's knee or ankle from among a set of pre-manufactured candidate products for knees or ankles based at least in part upon the leg circumference of the user; and an output device to display information received from the processor, the information identifying the recommended product to the user, wherein the foot mat is a pressure array foot mat, wherein the processor is in communication with the pressure array foot mat, the processor configured to receive a plurality of pressure measurements from the pressure array foot mat while the user stands thereupon, wherein the processor is configured to calculate an arch index of the user's foot, the processor further configured to select a recommended product for the user's foot from among a set of pre-manufactured candidate products for feet based at least in part upon the plurality of pressure measurements and arch index.

In an embodiment, the present invention is an apparatus, comprising: a foot mat; a depth sensing camera; an elevated foot platform that reduces or prevents rotational movement of a foot; a processor in communication with the depth sensing camera, the processor further configured to calculate the circumference of a user's leg based on data from the depth sensing camera while the user has one foot on the foot mat and one foot on the elevated foot platform, the processor further configured to select a recommended product for the user's knee or ankle from among a set of pre-manufactured candidate products for knees or ankles based at least in part upon the leg circumference of the user; and an output device to display information received from the processor, the information identifying the recommended product to the user, wherein the processor is adapted to infer the location of a leg joint of the user and calculate the circumference of the user's leg at a target distance from the inferred leg joint.

In an embodiment, the present invention is an apparatus, comprising: a foot mat; a depth sensing camera; an elevated foot platform that reduces or prevents rotational movement of a foot; a processor in communication with the depth sensing camera, the processor further configured to calculate the circumference of a user's leg based on data from the depth sensing camera while the user has one foot on the foot mat and one foot on the elevated foot platform, the processor further configured to select a recommended product for the user's knee or ankle from among a set of pre-manufactured candidate products for knees or ankles based at least in part upon the leg circumference of the user; and an output device to display information received from the processor, the information identifying the recommended product to the user, wherein the processor is adapted calculate the circumference of the user's leg while the user is in a first standing position and while the user is in a side standing position relative to the depth sensing camera, and wherein the processor is adapted to combine the two calculations to calculate a more accurate circumference of the leg.

In an embodiment, the invention is a process for identifying a recommended product to a user from among a set of pre-manufactured candidate products, the process comprising: providing an apparatus, comprising: a foot mat; a depth sensing camera; an elevated foot platform that reduces or prevents rotational movement of a foot; a processor in communication with the depth sensing camera, the processor further configured to calculate the circumference of a user's leg based on data from the depth sensing camera while the user has a first foot on the foot mat and a second foot on the elevated foot platform, the processor further configured to select a recommended product for the user's knee or ankle from among a set of pre-manufactured candidate products for knees or ankles based at least in part upon the leg circumference of the user; and an output device to display information received from the processor, the information identifying the recommended product to the user; and displaying information received from the processor, wherein the information received from the processor identifies the recommended product to the user for the user's knee or ankle from among a set of pre-manufactured candidate products for knees or ankles.

In an embodiment, the invention is a process for identifying a recommended product to a user from among a set of pre-manufactured candidate products, the process comprising: providing an apparatus, comprising: a foot mat; a depth sensing camera; an elevated foot platform that reduces or prevents rotational movement of a foot; a processor in communication with the depth sensing camera, the processor further configured to calculate the circumference of a user's leg based on data from the depth sensing camera while the user has a first foot on the foot mat and a second foot on the elevated foot platform, the processor further configured to select a recommended product for the user's knee or ankle from among a set of pre-manufactured candidate products for knees or ankles based at least in part upon the leg circumference of the user; and an output device to display information received from the processor, the information identifying the recommended product to the user; and displaying information received from the processor, wherein the information received from the processor identifies the recommended product to the user for the user's knee or ankle from among a set of pre-manufactured candidate products for knees or ankles, wherein the elevated foot platform comprises one, two, or three foot wells.

In an embodiment, the invention is a process for identifying a recommended product to a user from among a set of pre-manufactured candidate products, the process comprising: providing an apparatus, comprising: a foot mat; a depth sensing camera; an elevated foot platform that reduces or prevents rotational movement of a foot; a processor in communication with the depth sensing camera, the processor further configured to calculate the circumference of a user's leg based on data from the depth sensing camera while the user has a first foot on the foot mat and a second foot on the elevated foot platform, the processor further configured to select a recommended product for the user's knee or ankle from among a set of pre-manufactured candidate products for knees or ankles based at least in part upon the leg circumference of the user; and an output device to display information received from the processor, the information identifying the recommended product to the user; and displaying information received from the processor, wherein the information received from the processor identifies the recommended product to the user for the user's knee or ankle from among a set of pre-manufactured candidate products for knees or ankles, wherein the foot mat is a pressure array foot mat, wherein the processor is in communication with the pressure array foot mat, the processor configured to receive a plurality of quasi-dynamic pressure measurements from the pressure array foot mat while the user stands thereupon.

In an embodiment, the invention is a process for identifying a recommended product to a user from among a set of pre-manufactured candidate products, the process comprising: providing an apparatus, comprising: a foot mat; a depth sensing camera; an elevated foot platform that reduces or prevents rotational movement of a foot; a processor in communication with the depth sensing camera, the processor further configured to calculate the circumference of a user's leg based on data from the depth sensing camera while the user has a first foot on the foot mat and a second foot on the elevated foot platform, the processor further configured to select a recommended product for the user's knee or ankle from among a set of pre-manufactured candidate products for knees or ankles based at least in part upon the leg circumference of the user; and an output device to display information received from the processor, the information identifying the recommended product to the user; and displaying information received from the processor, wherein the information received from the processor identifies the recommended product to the user for the user's knee or ankle from among a set of pre-manufactured candidate products for knees or ankles, wherein the foot mat is a pressure array foot mat, wherein the processor is in communication with the pressure array foot mat, the processor configured to receive a plurality of quasi-dynamic pressure measurements from the pressure array foot mat while the user stands thereupon, wherein the processor is configured to calculate an arch index of the user's foot, the processor further configured to select a recommended product for the user's foot from among a set of pre-manufactured candidate products for feet based at least in part upon the plurality of pressure measurements and arch index, and wherein the information received from the processor identifies the recommended product to the user for the user's foot from among a set of pre-manufactured candidate products for feet.

In an embodiment, the invention is a process for identifying a recommended product to a user from among a set of pre-manufactured candidate products, the process comprising: providing an apparatus, comprising: a foot mat; a depth sensing camera; an elevated foot platform that reduces or prevents rotational movement of a foot; a processor in communication with the depth sensing camera, the processor further configured to calculate the circumference of a user's leg based on data from the depth sensing camera while the user has a first foot on the foot mat and a second foot on the elevated foot platform, the processor further configured to select a recommended product for the user's knee or ankle from among a set of pre-manufactured candidate products for knees or ankles based at least in part upon the leg circumference of the user; and an output device to display information received from the processor, the information identifying the recommended product to the user; and displaying information received from the processor, wherein the information received from the processor identifies the recommended product to the user for the user's knee or ankle from among a set of pre-manufactured candidate products for knees or ankles, wherein the processor is adapted to infer the location of a leg joint of the user and calculate the circumference of the user's leg at a target distance from the inferred leg joint.

In an embodiment, the invention is a process for identifying a recommended product to a user from among a set of pre-manufactured candidate products, the process comprising: providing an apparatus, comprising: a foot mat; a depth sensing camera; an elevated foot platform that reduces or prevents rotational movement of a foot; a processor in communication with the depth sensing camera, the processor further configured to calculate the circumference of a user's leg based on data from the depth sensing camera while the user has a first foot on the foot mat and a second foot on the elevated foot platform, the processor further configured to select a recommended product for the user's knee or ankle from among a set of pre-manufactured candidate products for knees or ankles based at least in part upon the leg circumference of the user; and an output device to display information received from the processor, the information identifying the recommended product to the user; and displaying information received from the processor, wherein the information received from the processor identifies the recommended product to the user for the user's knee or ankle from among a set of pre-manufactured candidate products for knees or ankles, wherein the processor is adapted calculate the circumference of the user's leg while the user is in a first standing position and while the user is in a side standing position relative to the depth sensing camera, and wherein the processor is adapted to combine the two calculations to calculate a more accurate circumference of the leg.

DETAILED DESCRIPTION

Figure 1:
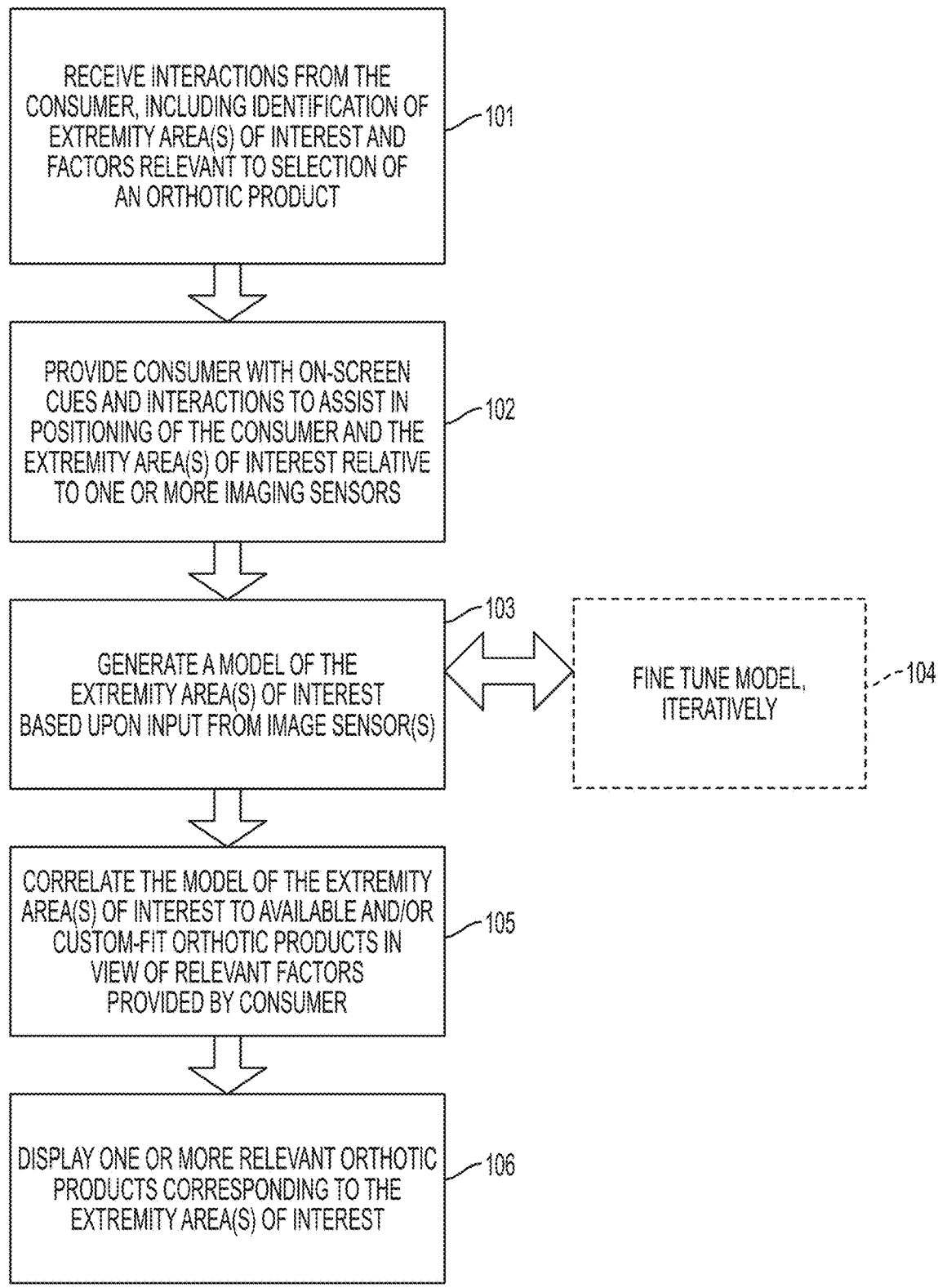
FIG. 1 illustrates a flowchart illustrating an embodiment of the present disclosure.

While methods, apparatuses, and computer-readable media are described herein by way of examples and embodiments, those skilled in the art recognize that methods, apparatuses, and computer-readable media for measuring a customer's physical attributes for the selection and/or manufacture of orthotic products are not limited to the embodiments or drawings described. It should be understood that the drawings and description are not intended to be limited to the particular form disclosed. Rather, the intention is to cover all modifications, equivalents and alternatives falling within the spirit and scope of the appended claims. Any headings used herein are for organizational purposes only and are not meant to limit the scope of the description or the claims. As used herein, the word "may" is used in a permissive sense (i.e., meaning having the potential to) rather than the mandatory sense (i.e., meaning must). Similarly, the words "include," "including," and "includes" mean including, but not limited to.

As is to be appreciated by those skilled in the relevant art, orthotic products may be placed under the foot, inside footwear, garments or other coverings or placed directly over major load bearing joints such as the ankle, knee, lower back, shoulder, neck, elbow and other joint areas extremities for the purpose of providing improved fit or comfort or structural support to the individual. Examples of orthotic products include insoles; foot cushions; heel cups; ankle braces, wraps, and tapes; knee braces, wraps, and tapes; elbow braces, wraps, and tapes; wrist braces, wraps, and tapes; etc. A consumer may want to quickly and accurately identify the proper orthotic product for their individual physical attributes. For example, a product may need to have the proper support, size, angular characteristics and functionality in connection with the person's weight, height or other sizing quality. Accordingly, retailers who make orthotic products available to consumers would want to be able to provide such a sizing or custom-fitting service to consumers without having to staff a person that has specialized training and/or knowledge of all possible products, and physical attributes, each of which being an independent variable.

In some possible embodiments of the disclosed invention, a kiosk measures a person's extremity and determines a recommended orthotic product for the person and the recommended product may be dispensed or may be selected by the person from the display. The measurements may be taken with a surface containing pressure sensors to measure a person's foot, to determine characteristics, including, but not limited to, weight, pressure points, foot length, foot geometry, etc. The kiosk may further query the person to obtain additional relevant information, such as planned activities and/or activity levels. A processor may, for example, correlate orthotic products to the person's foot measurements. In one example embodiment, the kiosk may contain a video screen that provides instructions to the person. The system may select a recommended orthotic product from among a set of candidate orthotic products based at least in part upon a plurality of pressure measurements received from the pressure sensors. The set of candidate orthotic products may be displayed on or near the kiosk in a merchandise display area, and the person may be provided with an indicia of the recommended orthotic product, such as a picture of the orthotic product, the model number of the orthotic product, a color symbol, shelf location, etc. The person may then easily locate the orthotic product that will provide the best calculated fit and support for the person's need in accordance with their individual physical attributes as calculated based on the inputs provided. Alternatively, products may be dispensed from a kiosk, for example, the kiosk may be configured as a vending machine. The orthotic product sold may be a pre-manufactured orthotic, and the set of candidate orthotic products may be a set of different models of pre-manufactured orthotics of varying attributes, such as size, arch support levels, arch index, cushioning levels (i.e. foam density, cushioning material used, etc.), etc. The range of models provided may be chosen to address the most common conditions needing an orthotic product, while coming in range of sizes and models needed to fit and provide an appropriate support level for the vast majority of the potential user population. Alternatively, in the case that the person's physical attributes require an orthotic product not available at the retail location or one which is not within the set of those appropriate for the vast majority of the potential user location, the kiosk may interface with an ordering system via a communications means to request that a conforming orthotic product be manufactured in accordance with the physical attributes of the person, or to identify other sales locations at which that particular orthotic product is available.

Measurements for upper and lower extremities may be achieved utilizing a variety of measurement functions, including the pressure sensor measurements described above. In an embodiment, one or more imaging sensors may be utilized to generate two-dimensional or three-dimensional models of the extremity-of-interest (i.e., the target extremity). By way of non-limiting example, the kiosk may be configured to include an imaging sensor that is capable of scanning an extremity (e.g., an ankle or knee) and generate a three-dimensional volumetric model of the target extremity, such as through determining a three dimensional surface for the portion of the extremity and/or joint of interest, and extrapolating the reverse side of the extremity and/or joint of interest to obtain the three dimensional model of the extremity and/or joint of interest. The imaging sensor may operate in one or more modes, including, but not limited to, infrared imaging, range imaging, ultrasound imaging, or any other mechanism known in the art that utilizes backscatter data to determine relative distance and characteristics of a targeted area. The data received by the imaging sensor may be used by a processor to generate a three-dimensional curvilinear map of the extremity of interest. Further, a combination of imaging sensors, whether sharing a single housing or not, may provide input to the generation of the three-dimensional model of the extremity of interest. By way of further non-limiting example, a plurality of two-dimensional images of the extremity of interest may be taken, each a sagittal slice of the extremity of interest, and then combined by the processor to generate a curvilinear model or map of the extremity of interest. In each case, the generated model or mapping of the extremity of interest may be used as an input to the processor for the purpose of the correlating the person's physical attributes to orthotic products, whether in-stock at the retailer or requiring the ordering of a custom-fit product.

As is to be appreciated by those skilled in the relevant art, garments are a challenge in obtaining accurate measurements of a person's extremities. In the case that a consumer is wearing shorts or loose fitting garments that can be pulled up to expose the extremity (e.g., knee), a more accurate measurement by imaging sensor can be accomplished. However, in the case that the consumer is wearing garments (e.g. pants, sweaters, etc.) and the processor detects the presence of such garments (e.g., based upon color, patterns, irregular shape, user input, slope), the processor may take into account the excess surface provided by those garments, and extrapolate the true physical attributes of the extremity of interest. Accordingly, a database of garment characteristics may be provided, which, in an embodiment, may be used by the processor to deduce excess surface area from a first generated model of the extremity of interest. It is further disclosed that the processor may categorize the detected garment in various categories, each of which provides a weight by which the first generated model of the extremity of interest is adjusted. By way of non-limiting example, the categories may include the material of the garment fabric, the fit of the garment (e.g., loose, tight) or whether the garment is an outer layer or inner layer garment. In order to avoid over (or under) compensation for garment layers and to provide accurate measurements, the processor may be provided with limits or rules by which further deductions in the surface area of the model or mapping are halted, e.g., the generated model does not conform with the vast majority of the potential user population.

In a further embodiment, a primary imaging sensor may be provided on the kiosk at a location relative to the average knee height (or average height/location of a different area of interest for an extremity) of the vast majority of the potential user population such that the knee or other relevant area of an upper or lower extremity is within the field of view of the imaging sensor. The imaging sensor may be configured to pivot or slew as needed to include the extremity of interest in its field of view. The primary imaging sensor may further be positioned at any location such that the extremity area of interest can be put in its field of view by requiring the person to move back from or towards the imaging sensor. In an embodiment, the imaging sensor may be positioned at a fixed location relative to the average pelvis height of the vast majority of the potential user population. The imaging sensor may be provided with a wide field of view and/or may be configured to mechanically pivot or slew to encompass a different field of view relative to its initial location.

In an embodiment, a plurality of imaging locations may be provided in the kiosk. That is, by way of non-limiting example, step-up bars, elevated platforms and hand-holds may be provided in order to facilitate the positioning of the extremity area of interest within the field of view of the imaging sensor(s), or to allow a wide field of view imaging system to prioritize analysis of the proper extremity and/or joint of interest. Step-up bars, elevated platforms and hand-holds may be stationary or controlled by mechanical means to provide fine tuning for the positioning of the extremity area of interest relative to the imaging sensor's field of view. For example, a step-up bar may be provided that, upon the person placing their foot on the bar, the knee is positioned within the field of view of the imaging sensor, or multiple step-up bars of varying heights may be provided such as to facilitate measurements of a variety of physical characteristics belonging to the potential user population. In addition, in an embodiment, the step-up bar may be configured in such a manner that the consumer's use of the step-up bar causes the consumer's knee to be placed at an angle to allow accurate imaging and/or measurements as an input to the model, and identify characteristics of the knee above and below its forward features. Further, elevated platforms may be provided that, upon the person placing their foot on the platform, the ankle is positioned within the field of view of the imaging sensor, or multiple platforms may be provided, or a platform may be of adjustable height by manual or mechanical means, wherein the mechanical means is controlled by the processor and the fine tuning adjustment is based on the first generated model of an extremity area of interest. Further, one or more hand-holds may be provided and each may be located centrally to the kiosk or to the left or right side to encourage use with the person's corresponding or opposite hand, each of which, upon the person holding the hand-hold, an extremity area of interest is positioned within the field of view of the imaging sensor; for example, a person's elbow. The hand-holds may provide a secondary (or primary, as may be the case) purpose to allow the person to stabilize themselves in a safe manner while utilizing a step-bar or elevated platform or other positioning means. In similar fashion to step-up bars, hand-holds may be configured so that a consumer' use of the hand-hold causes the consumer's elbow or wrist to be placed at an angle that allows for more accurate measurements and imaging as an input to the model.

In an embodiment, a plurality of imaging sensors may be provided, each configured to have a different field of view that is relevant to and ideally situated relative to one or more extremity and/or point area of interest. Each of the plurality of imaging sensors may operate independently to provide input to the processor, or as a combination of sensors to provide multiple inputs from different vantage points relative to an extremity area of interest as multiple input sources to the processor. One or more of the image sensors may be configured for the purpose of assisting the consumer in orienting themselves properly on the kiosk area, relative to the kiosk area or as a source for interactive or entertainment cues to be provided to the consumer. By way of non-limiting example, an image sensor may be provide input to the processor for the purpose of capturing a consumer's attention as a marketing or advertising mechanism as the consumer traverses the kiosk area, providing a full body image of the consumer upon which one or more relevant or potentially relevant orthotic products may be overlayed by the processor, or providing a consumer location reference information relative to the kiosk from which the processor may generate positioning cues and interaction instructions that may be provided to the consumer via the display.

In an embodiment a display or video screen is provided which is configured to present visual cues, interactions, instructions, images, image sensor feeds, extremity models, consumer input requests to the consumer. In an embodiment, the display may be a capacitive touch interface or other device as are known in the art to be capable of both displaying content and receiving using input. In some embodiments, other input mechanisms may be used as well; for example, a keyboard, mouse, stylus, non-contact gesture control, oral control or other similar interface device. Further embodiments may include wireless communication, either by way of the Internet or local communication means (e.g. Bluetooth) to interact with and display information to a device that is in the consumer's possession (e.g., a smartphone, tablet, etc.).

In an embodiment, the consumer is provided a cue generated by the processor and presented via the display to approach the kiosk. The processor may present via the display a real-time image or video of the consumer to assist the consumer in proper positioning on or relative to the kiosk. The processor may present a pre-written script to the user via the display to assist the consumer in orienting themselves to the capabilities of the system, and determining the realm of relevant orthotic products that the individual consumer may have a need for. For example, the consumer may be provided an interface by the processor that requests the consumer to select different areas of a skeletal mapping of a generic consumer or the individual consumer (as provided by one or more of the imaging sensors). The selected areas of the skeletal mapping may correlate to one or more extremity areas for which orthotic products are available. For example, the consumer may be prompted to select foot, knee or ankle as the extremity area of interest, and then answer certain relevant questions; such as, "How long have you had the injury?", "Is it a recurring injury?", "Do you have swelling?", "What activities will you be doing while wearing a brace?" Upon input of such relevant factors, the consumer may be prompted to place the relevant foot corresponding to the relevant extremity area of interest on the elevated platform, step-up bar or pressure sensor to begin the process of determining the ideal orthotic product. In an embodiment, the consumer may be prompted to roll or pull up their pants in order to expose an ankle to the relevant imaging sensor, or, in the case that the extremity area of interest is a knee, to tighten their pants around the knee by using their hands. The processor, receiving imaging input corresponding to the extremity area of interest from the imaging sensor, may generate further visual cues for display in order to instruct the consumer to reposition the extremity, move closer or further back relative to the imaging sensor, further expose an extremity, further tighten a garment, or present errors to the consumer. Further visual cues may be provided, as is to be appreciated by those skilled in the relevant art.

FIG. 1 is flowchart showing a method for receiving input from a consumer and generating an orthotic product recommendation. At step 101, interactions are received by the processor from the input means, which may be, but is not limited to, a touch sensitive capacitive display screen. The information received may be provided in response to visual cues presented by the processor by way of the display. Requests include, but are not limited to, information regarding the consumer, such as activity level, pain history, ability to stretch an extremity, comfort parameters, identification of extremity areas of interest as they relate to orthotic product selections. The consumer may be provided with a display interface that allows them to select extremity areas of interest. At step 102, the consumer is provided with on-screen cues generated by the processor and presented by means of the display. The cues include instructions and feedback on how the consumer may position the one or more extremity areas of interest within the field of view of one or more of the imaging sensors. The consumer may also be presented instructions on how to expose the relevant extremity or adjust garments, as may be appropriate. At step 103, the processor receives the imaging data from the one or more imaging sensors concerning the extremity area of interest and generates a first model of the extremity area of interest. The processor may provide feedback based on the success or relative failure and/or accuracy of the first model to the consumer in order to relate instructions on consumer positioning relative to the imaging sensors or adjustment of garments. At step 104, the processor may iteratively fine tune the first model by way of additional imaging data received from the imaging sensors as a result of the feedback related to the consumer. At step 105, the processor may correlate the model of the extremity area(s) of interest and the personal factors provided by the consumer (e.g., activity level, etc.) with the orthotic products available in order to determine a best-fit. The best-fit selection may require the processor to select an orthotic product that is as close a match as possible to the model (for example, if the only sizes available are small, medium, large, etc.). In some embodiments, the processor may determine that a custom-fit product is preferable to the consumer in comparison to the available orthotic products at the retailer. At step 106, the processor, by the display, presents the one or more orthotic products that are recommended for the consumer for the extremity area of interest.

Figure 2:
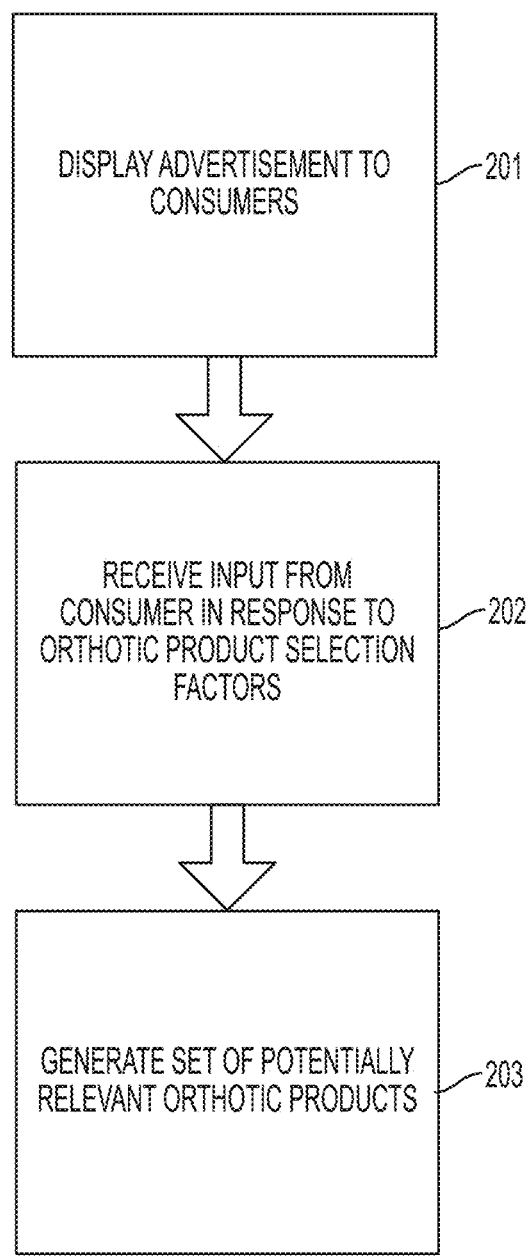
FIG. 2 illustrates a flowchart illustrating an embodiment of the present disclosure.

FIG. 2 is flowchart showing a method for displaying an advertisement or other message to the consumer, receiving input from a consumer and generating a set of potentially relevant orthotic product that correlate to the input received. At step 201, an advertisement is displayed to a consumer, who may not be actively engaged with the system or kiosk. For example, the consumer may be traversing the field of view of an imaging sensor, and the processor may then overlay orthotic product images over the image of the traveling consumer, thereby catching their attention. At step 202, upon the consumer being engaged by the system or kiosk, the consumer may be prompted to provide input as to their orthotic product needs, pain areas and activity history. At step 203, based upon the provided input and passively collected imaging data of the consumer (including any models of the consumer generated based on information received from the one or more imaging sensors), a set of potentially relevant orthotic products may be generated and presented to the consumer.

Figure 3:
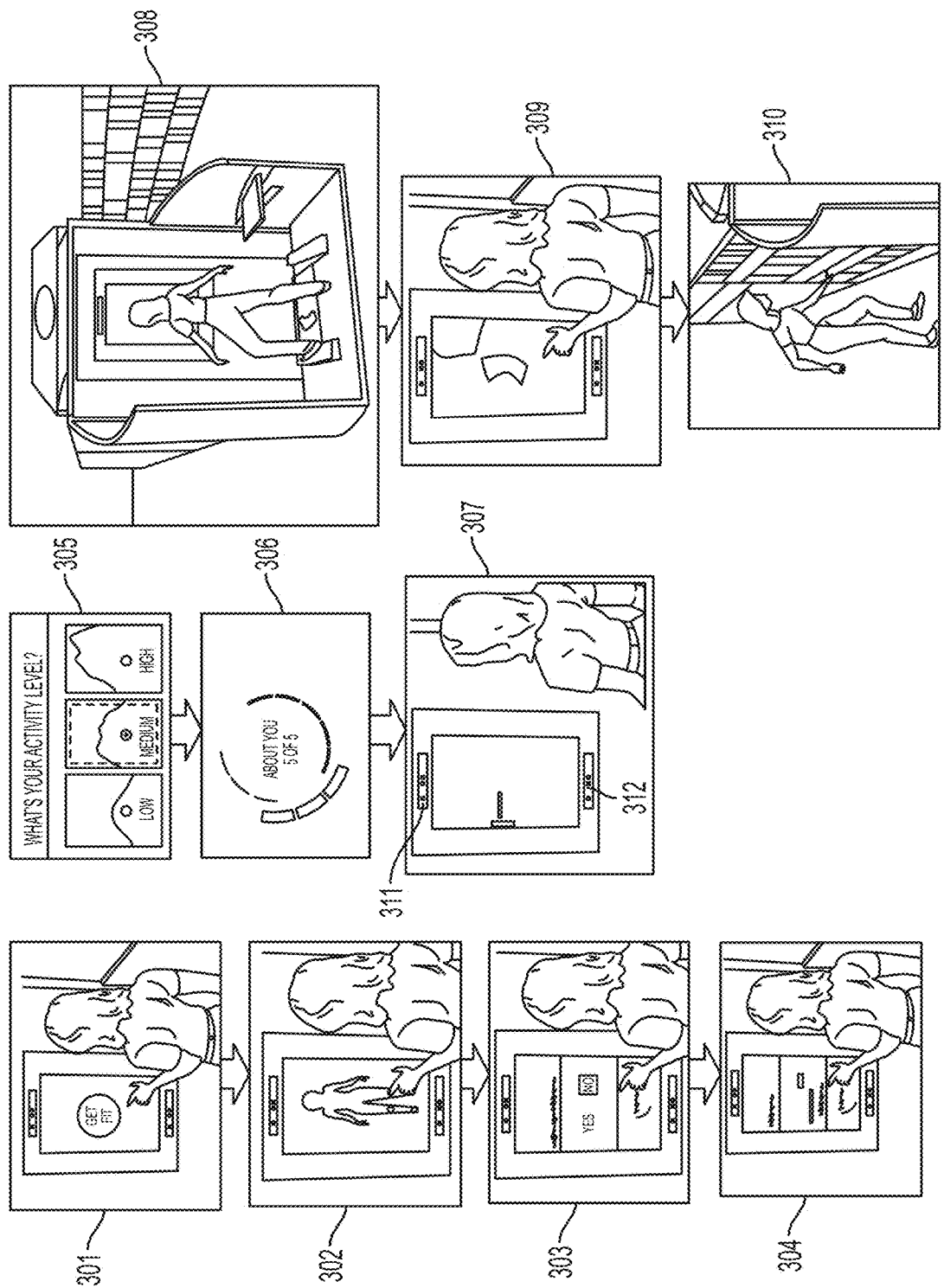
FIG. 3 illustrates a flowchart illustrating an embodiment of the present disclosure, user interfaces of the present disclosure, and an embodiment of the kiosk structure of the present disclosure.

FIG. 3 is a flow chart showing a system and method for receiving consumer input, generating a model for one or more extremity areas of interest, and presenting a recommended orthotic product correlating to the available information. At step 301, the system receives an initial interaction from a consumer in response to a "Get Fit" graphic, or other advertisement. At step 302, the consumer selects the extremity areas of interest for which they are interested in receiving orthotic product recommendations. In this example, the consumer has selected the right knee by way of a capacitive touch screen input device. At step 303, the consumer is prompted to answer one or more questions corresponding to injury history, activity history or other relevant input data. For example, the consumer is prompted to answer "Is this a recurring injury?" At step 304, the consumer is presented with an interface through which they can indicate the level of pain associated with the extremity area of interest. At step 305, the consumer is presented with an interface through which they can indicate their "activity level". At step 306, a progress screen is presented to the consumer to indicate their progress in completing the "About You" interactive session. At step 307, the consumer is presented the instruction "Step Back" so that they can be positioned within the field of view and/or range of the one or more imaging sensors, 311 and 312, as each may be relevant to a selected extremity area of interest. At step 308, the consumer is presented with instructions to position their knee on a step-up bar or elevated platform such that their knee, an extremity area of interest, is positioned within the field of view of one or more of the imaging sensors. As shown, a plurality of step-up bars or elevated platforms may be provided for the purpose of proper positioning of an extremity area of interest. The height and location of each of these positioning aids may be adjusted. Further, they may be provided with an angular slope such that individuals of varying height can position their foot or other extremity on the portion of the slope that best puts the extremity of interest within the field of view and/or range of the relevant imaging sensor(s). At step 309, the processor generates an orthotic product recommendation based upon a model that was generated using the input received from the imaging sensors. At step 310, the consumer follows the instructions and recommendations provided by the processor and selects the corresponding orthotic product, which may be color-coded to correspond to the recommendation presented via the display.

Figure 4:
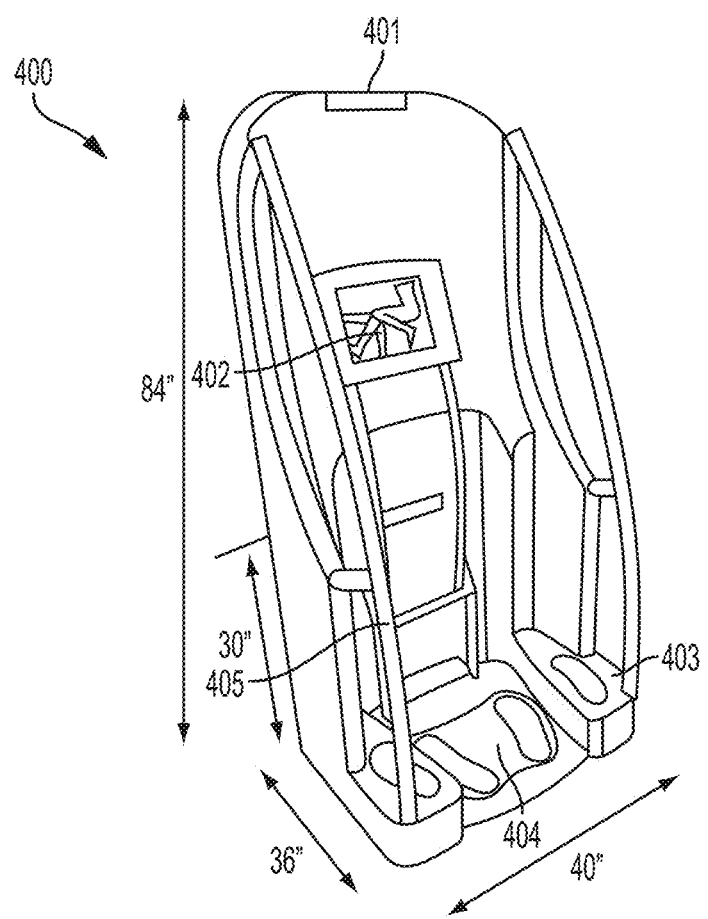
FIG. 4 illustrates an embodiment of the kiosk structure of the present disclosure.

Referring now to FIG. 4, a kiosk apparatus 400 is shown, configured to provide a plurality of imaging sensors 401, a display 402, an elevated platform 403, a pressure sensitive platform 404, and a plurality of hand-holds 405. The pressure sensitive platform may be utilized to receive pressure information and physical attributes corresponding to a consumer's foot/feet, as well as other relevant information, such as weight and/or the positioning of the consumer. The elevated platform(s) may be provided at a variety of locations and at a variety of heights. They may further be capable of being manually or mechanically adjusted or automatically mechanically adjusted. The hand-holds may be provided as a means of providing stabilization to the consumer as they utilize an elevated platform or other structure disclosed herein. The hand-holds may further provide grips, or indicia useful to positioning upper extremities of interest relative to an imaging sensor.

Figure 5:
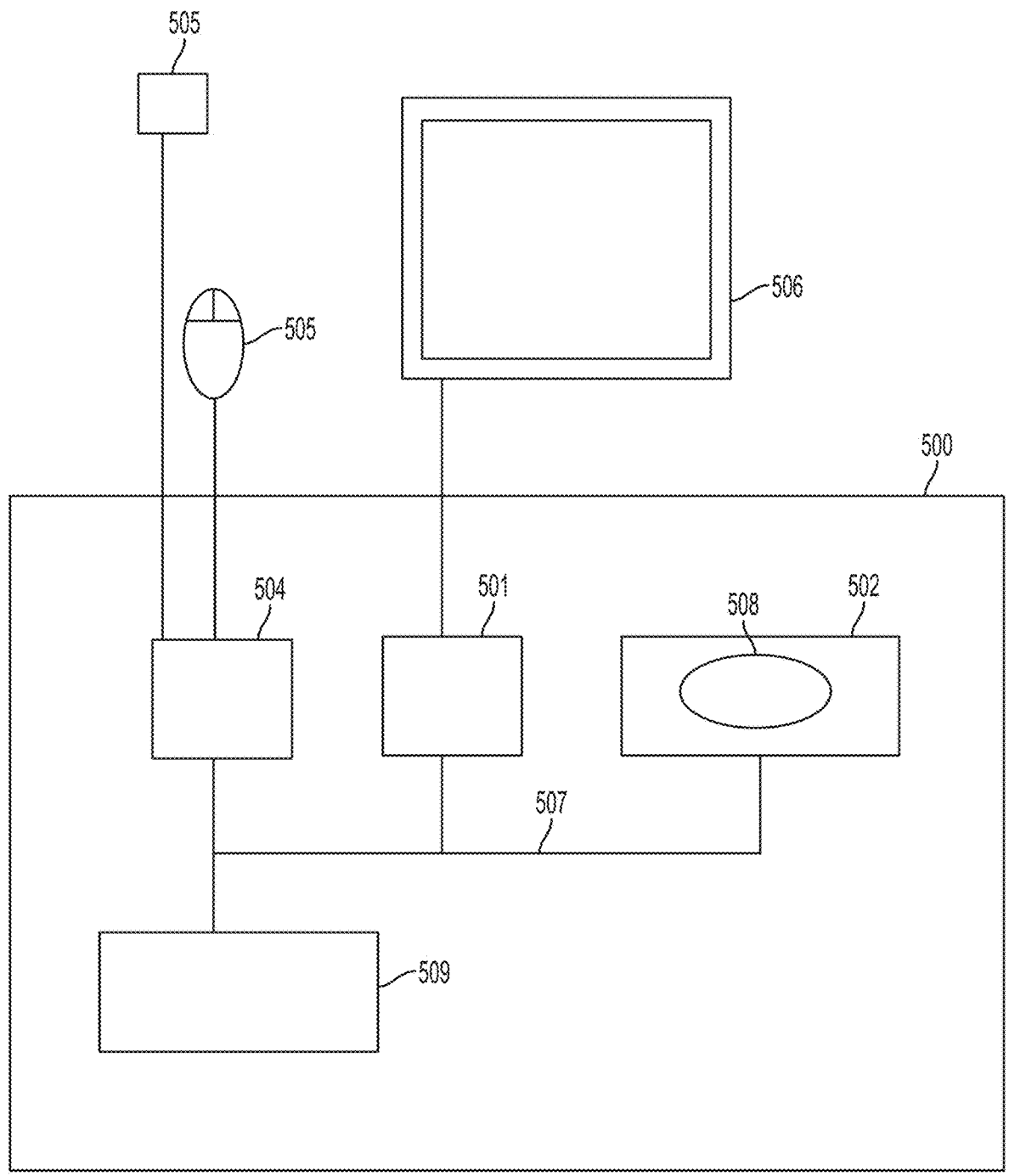
FIG. 5 illustrates an embodiment of the computer-implemented system of the present disclosure.

With reference to FIG. 5, the computing environment 500 includes at least one processing unit 501 and memory 502. The processing unit 501 executes computer-executable instructions and may be a real or a virtual processor. In a multi-processing system, multiple processing units execute computer-executable instructions to increase processing power. The memory 502 may be volatile memory (e.g., registers, cache, RAM), non-volatile memory (e.g., ROM, EEPROM, flash memory, etc.), or some combination of the two. The memory 502 may store software instructions 508 for implementing the described techniques when executed by one or more processors. Memory 502 can be one memory device or multiple memory devices.

A computing environment may have additional features. For example, the computing environment 500 includes storage 504, one or more input devices 505, one or more output devices 506, one or more imaging sensors or other sensor devices 503, and one or more communication connections 509. An interconnection mechanism 507, such as a bus, controller, or network interconnects the components of the computing environment 500. Typically, operating system software or firmware (not shown) provides an operating environment for other software executing in the computing environment 500, and coordinates activities of the components of the computing environment 500.

The storage 504 may be removable or non-removable, and includes magnetic disks, magnetic tapes or cassettes, CD-ROMs, CD-RWs, DVDs, or any other medium which can be used to store information and which can be accessed within the computing environment 500. The storage 504 may store instructions for the software 508.

The input device(s) 505 may be a touch input device such as a keyboard, mouse, pen, trackball, touch screen, or game controller, a voice input device, a scanning device, a digital camera, remote control, or another device that provides input to the computing environment 500. The output device(s) 506 may be a display, television, monitor, printer, speaker, or another device that provides output from the computing environment 500.

The communication connection(s) 509 enable communication over a communication medium to another computing entity. The communication medium conveys information such as computer-executable instructions, audio or video information, or other data in a modulated data signal. A modulated data signal is a signal that has one or more of its characteristics set or changed in such a manner as to encode information in the signal. By way of example, and not limitation, communication media include wired or wireless techniques implemented with an electrical, optical, RF, infrared, acoustic, or other carrier.

Implementations can be described in the general context of computer-readable media. Computer-readable media are any available media that can be accessed within a computing environment. By way of example, and not limitation, within the computing environment 500, computer-readable media include memory 502, storage 504, communication media, and combinations of any of the above.

Of course, FIG. 5 illustrates computing environment 500, sensor device 503, display device 506, and input device 505 as separate devices for ease of identification only. Computing environment 505, display device 506, and input device 505 may be separate devices (e.g., a personal computer connected by wires to a monitor and mouse), may be integrated in a single device (e.g., a mobile device with a touch-display, such as a smartphone or a tablet), or any combination of devices (e.g., a computing device operatively coupled to a touch-screen display device, a plurality of computing devices attached to a single display device and input device, etc.). Computing environment 500 may be a set-top box, mobile device, personal computer, or one or more servers, for example a farm of networked servers, a clustered server environment, or a cloud network of computing devices.

Example 1

Figure 6:
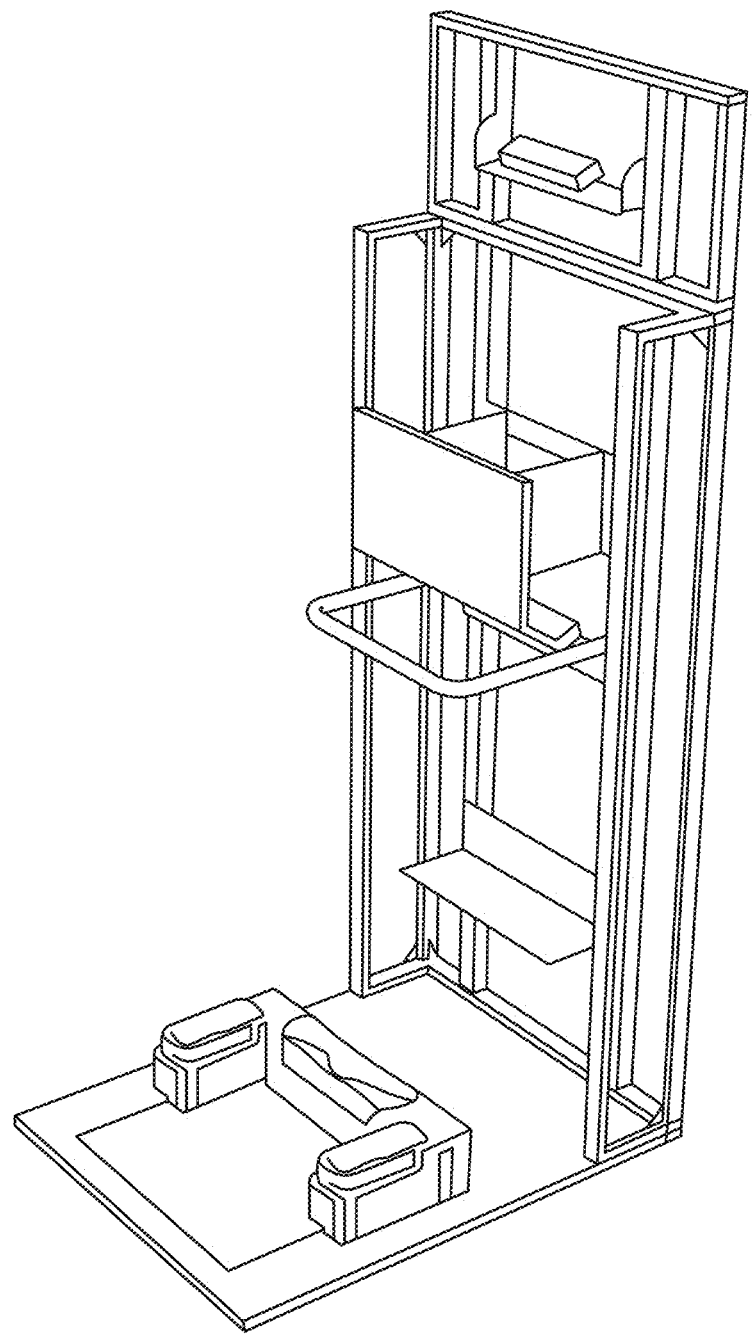
FIG. 6 illustrates an Example of the kiosk of the present disclosure.
Figure 7:
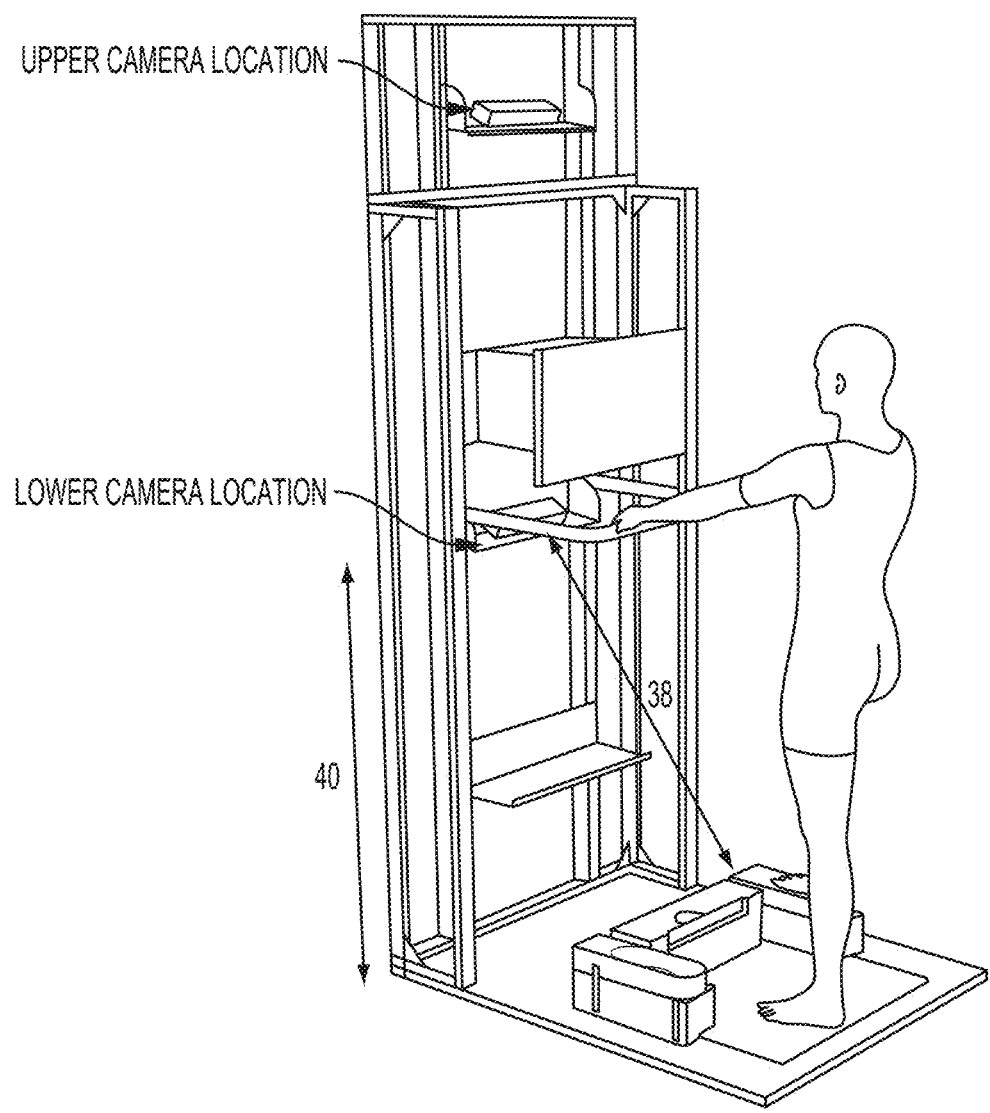
FIG. 7 illustrates an Example of the kiosk of the present disclosure.
Figure 8:
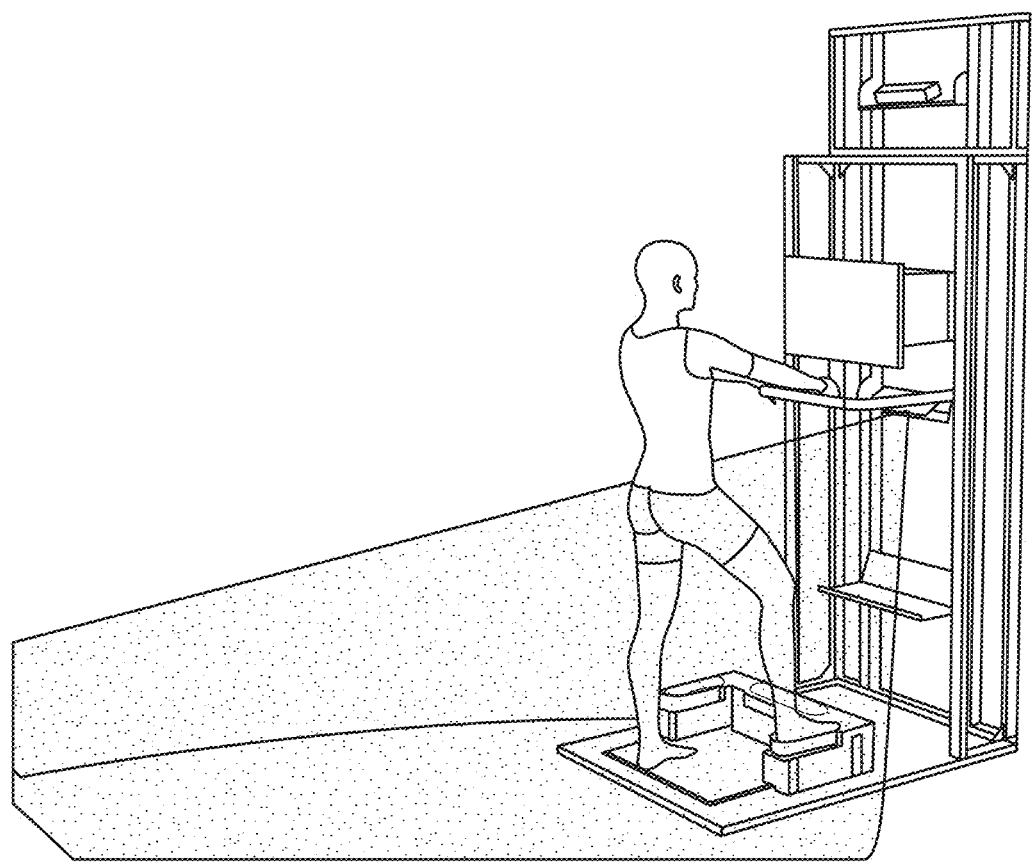
FIG. 8 illustrates an Example of the kiosk of the present disclosure.
Figure 9:
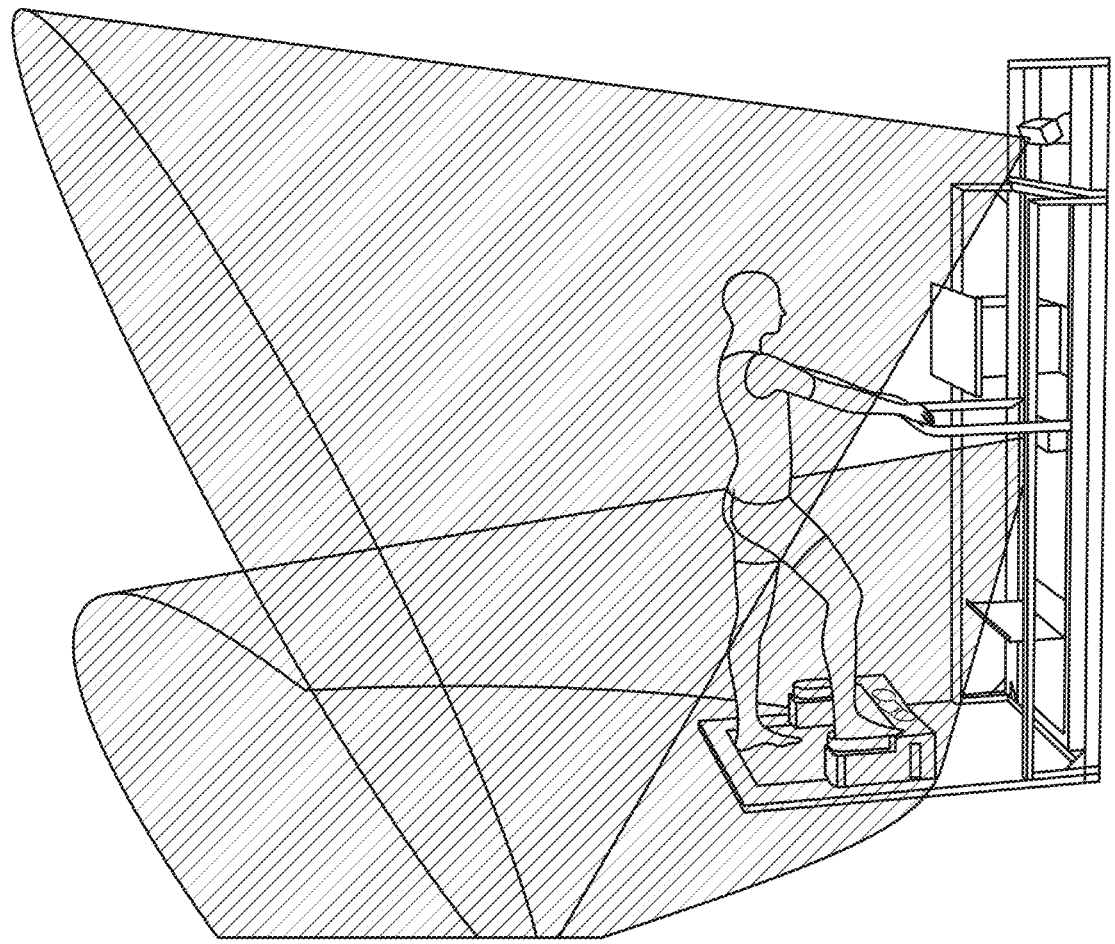
FIG. 9 illustrates an Example of the kiosk of the present disclosure.

A depth-sensing camera (preferably Microsoft Kinect version 2) is mounted on a test rig (FIG. 6). The Kinect V2 camera is mounted approximately 40" from the base and 38" from the foot step (FIG. 7). The sensor mounted in this position allows a lower body field of view up to mid torso (FIG. 8). A second sensor may be mounted to the kiosk (FIG. 9).

Figure 10:
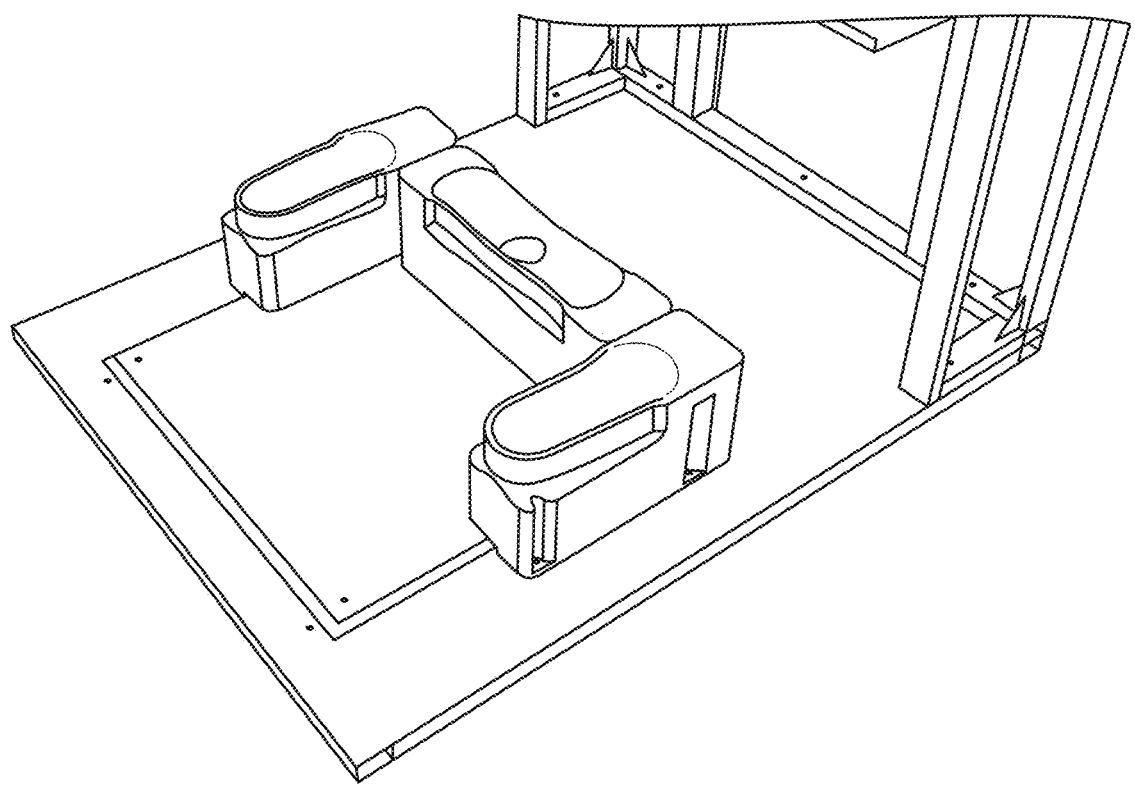
FIG. 10 illustrates an elevated foot platform of the kiosk of the present disclosure.

Variable placement of the foot and leg prohibits accurate and reproducible measurement of the circumference of the leg, ankle, and foot. To mitigate this, we invented a elevated foot platform (FIG. 10) that guides foot and leg placement and allows for a consistent measuring process. The elevated foot platform reduces or prevents the user from rotating the foot of the leg to be measured, but does not interfere with the measurement process. Preferably, the elevated foot platform comprises at least one foot wells, and more preferably three foot wells (one for each of the left and right feet in the front scanning position, and one for either of the left or right feet in the side scanning position).

To infer the position of the knee joint, the user's leg is scanned in a bent leg stance with the legs sufficiently spaced apart to develop a dimensionally accurate and appropriate model from which knee and/or ankle wraps can be recommended to the user.

Figure 11:
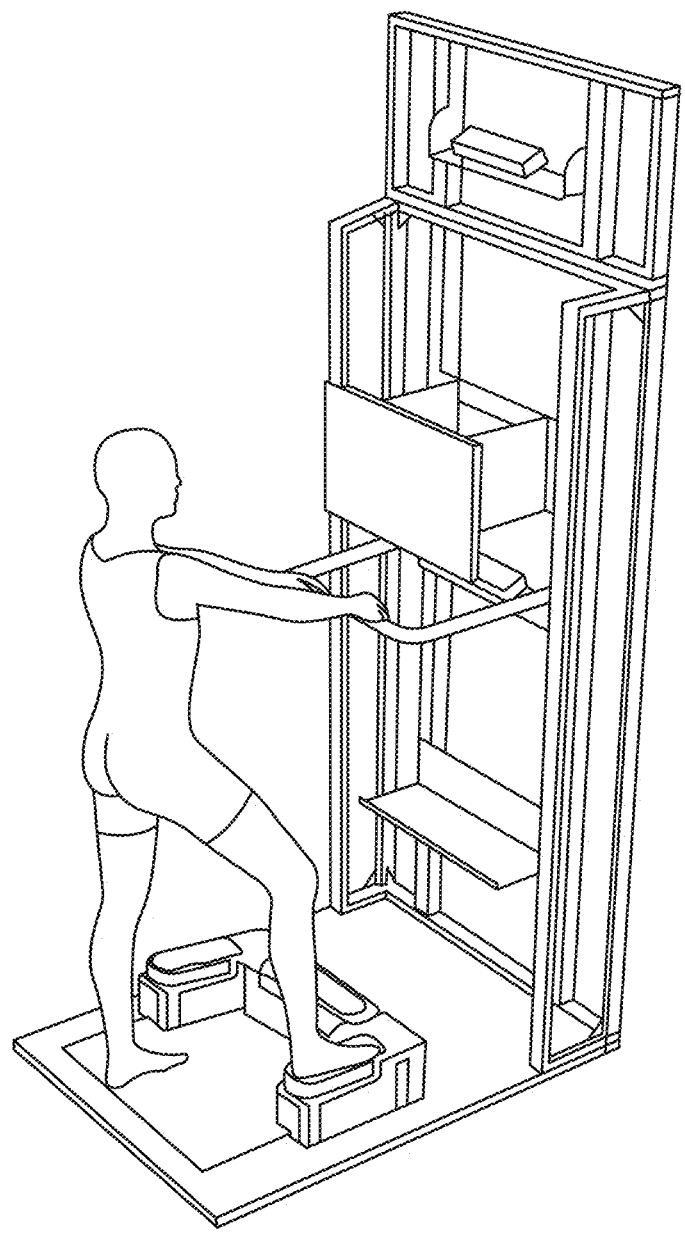
FIG. 11 illustrates an Example of the kiosk of the present disclosure.
Figure 12:
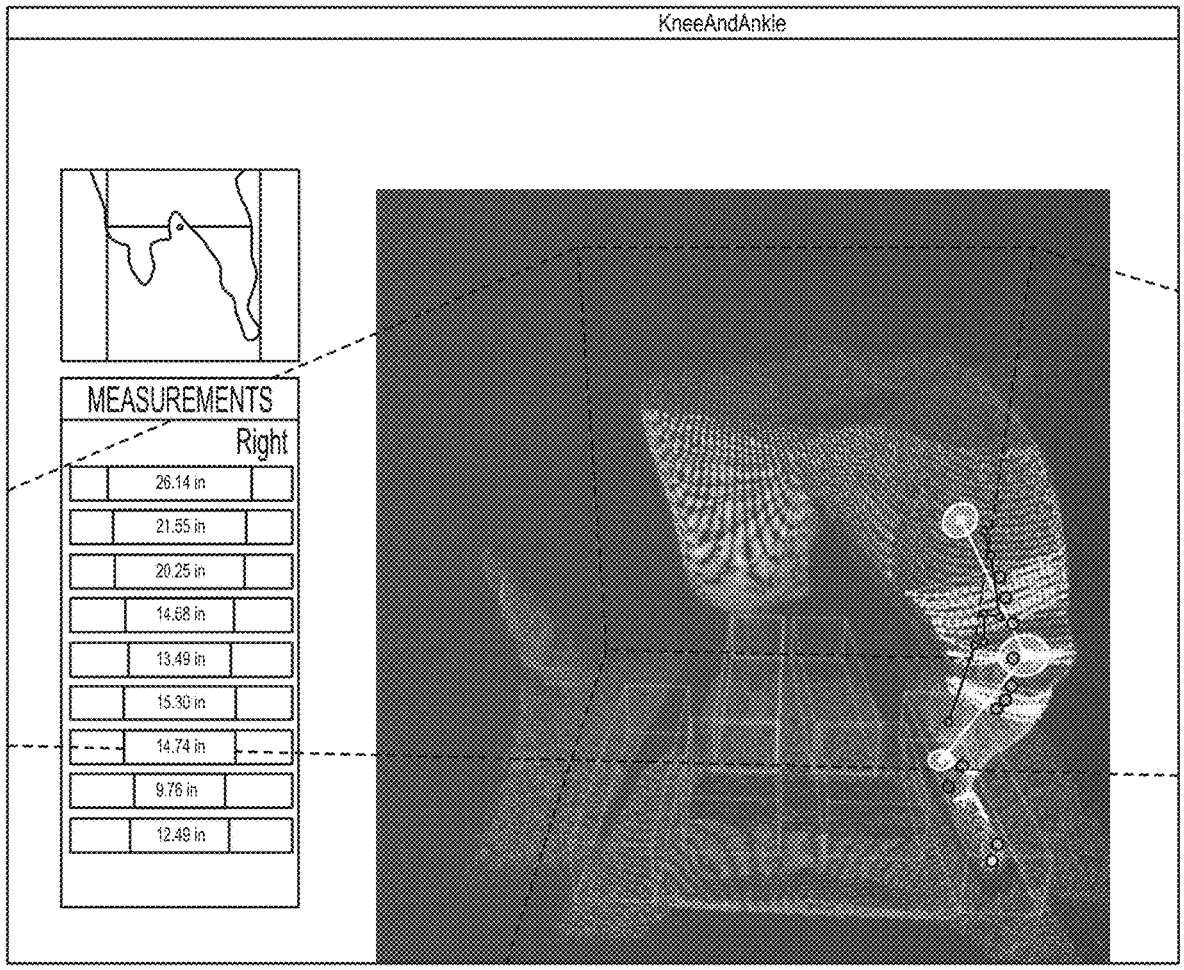
FIG. 12 illustrates an on-screen display of the kiosk of the present disclosure.

Initially, a user is positioned in a front scanning position in which the user is positioned with both feet located on a foot mat sensor array to verify a planted-feet position. For the next step, the user places the foot of the leg to be measured on the elevated platform (FIG. 11). On-screen, the user is shown, in real time, a point cloud of the user's leg with further instructions for the user to move the leg to a fixed position relative to the sensor for measurement (FIG. 12). Once the user moves the leg to an appropriate position for measurement, the knee joint location can be inferred, target distances away from the inferred knee joint can be determined (e.g., 5 inches above and 5 inches below the inferred knee joint), and the circumferential curves of the upper and lower leg at the respective target distances from the inferred knee joint are calculated.

Based on the calculated circumferences of the upper and lower leg at the target distances (above and below the inferred knee joint, respectively), the system ultimately recommends a knee brace for the user. Preferably, the recommended knee brace for the user is immediately available to the user at the point of sale.

Figure 13:
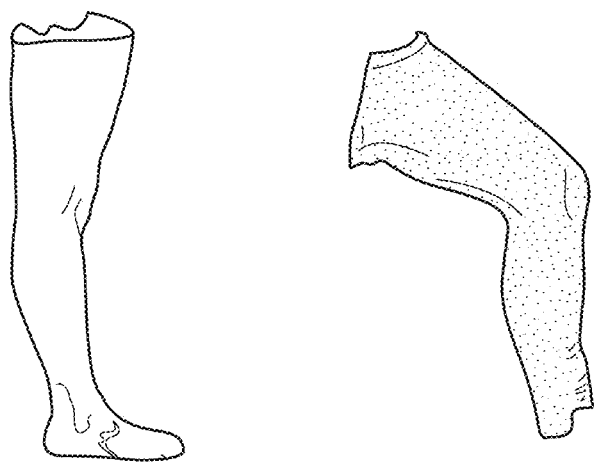
FIG. 13 illustrates leg asymmetry from standing to bent leg stance (asymmetry increases with increased BMI).
Figure 13:
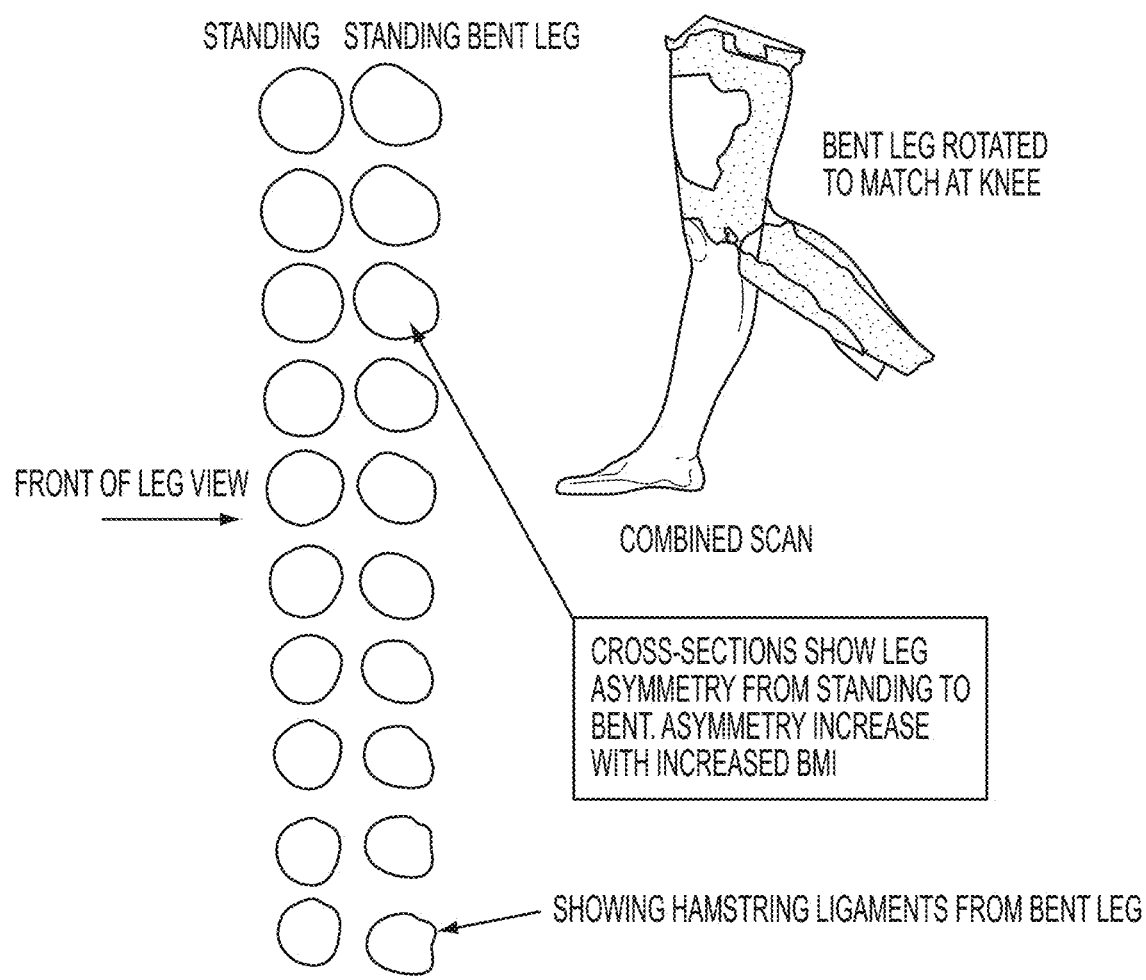
Figure 14:
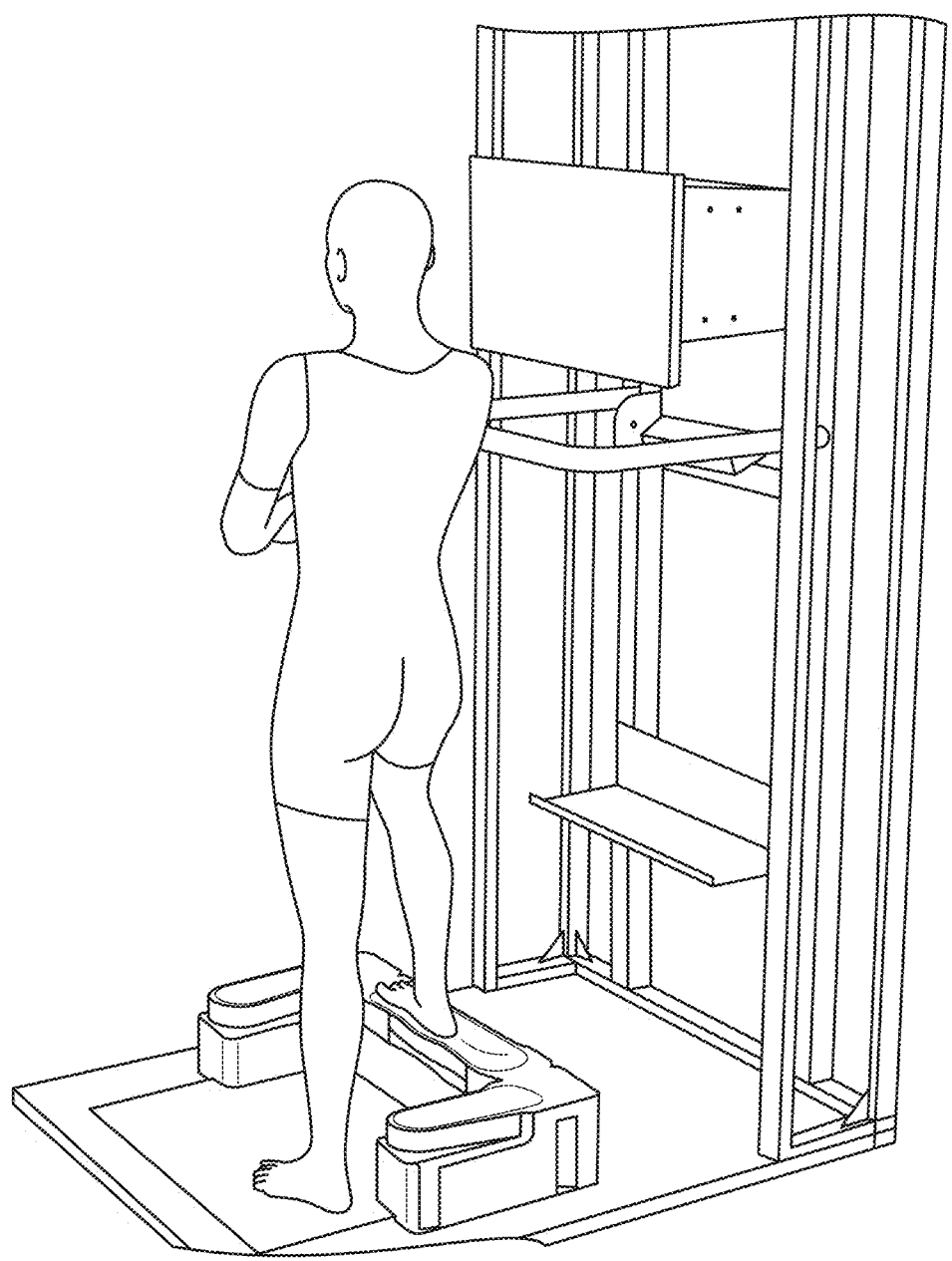
FIG. 14 illustrates an Example of the kiosk of the present disclosure.
Figure 15:
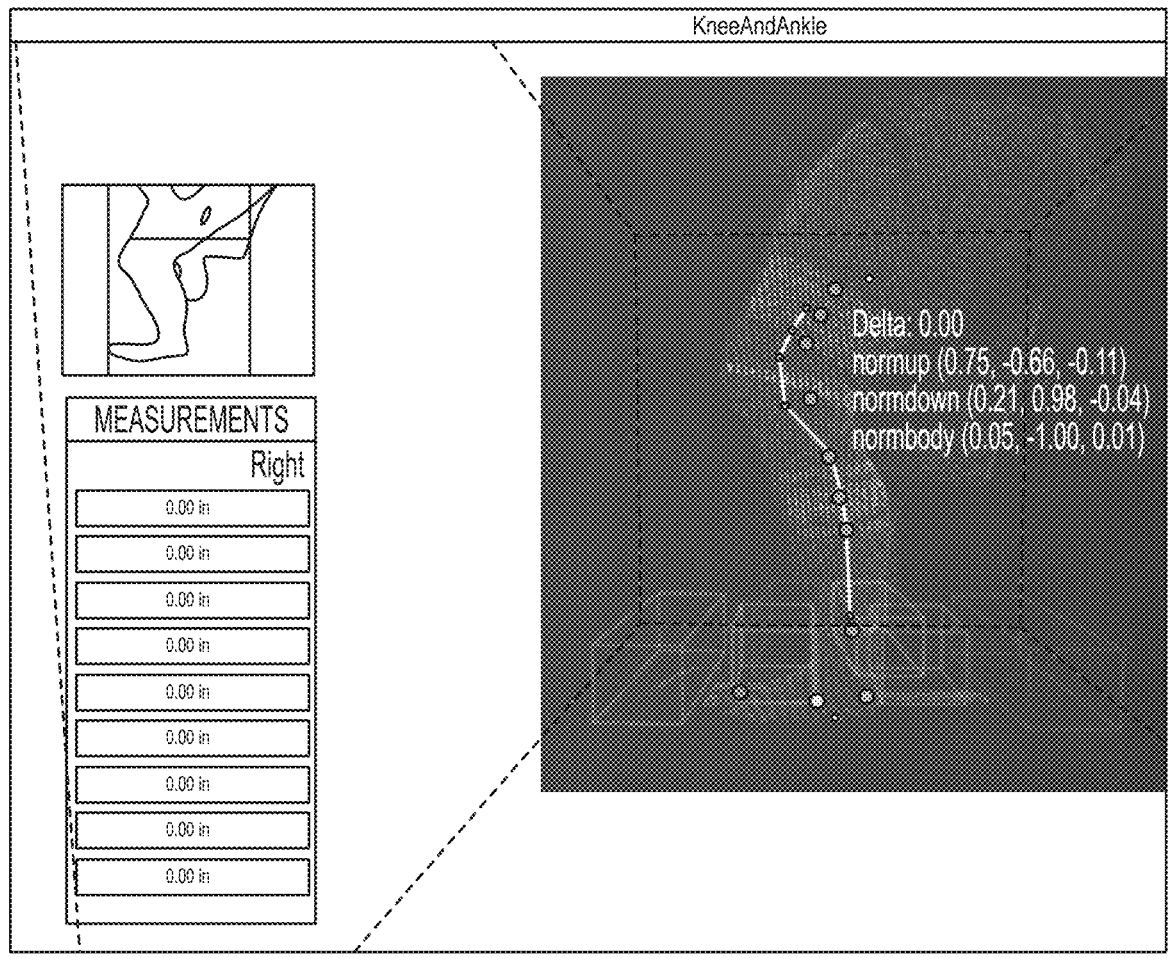
FIG. 15 illustrates an on-screen display of the kiosk of the present disclosure.

Since leg mass shape may change significantly between a standing position and a bent-knee position with increasing Body-Mass Index (BMI), the front scanning position alone may lead to an incorrect sizing recommendation (FIG. 13). For further enhanced accuracy, a measurement process according to the present invention may further comprise a matching measurement with the user in a side scanning position (FIG. 14). Similar to the front scan, for a side measurement, both feet are first placed on the pressure array mat for positive location of the feet to ensure that the legs are suitably separated and that the user is balanced, after which the foot of the leg to be measured is placed on the elevated foot platform. Again, the user is guided to place the leg an appropriate measurement position. If the side scanning position is the first measurement position, once the data is captured in the side scanning position (FIG. 15), the user is re-positioned to a front scanning position where the front measurement is captured. Alternatively, the front measurement may be captured first followed by the side measurement. The two calculations or measurements are combined to calculate a more accurate circumference of the leg.

Depending on the type of clothing the user is wearing. There may be some mitigation of clothing to limit the interference with the scan. The user may be asked to grab the clothing and smooth it to remove wrinkles or stretch it in a certain direction to allow for a better scan of the leg profile.

Having described and illustrated the principles of our invention with reference to the described embodiment, it will be recognized that the described embodiment can be modified in arrangement and detail without departing from such principles. It should be understood that the programs, processes, or methods described herein are not related or limited to any particular type of computing environment, unless indicated otherwise. Various types of general purpose or specialized computing environments may be used with or perform operations in accordance with the teachings described herein. Elements of the described embodiment shown in software may be implemented in hardware and vice versa.

The invention claimed is:

1. An apparatus, comprising: a foot mat; a depth sensing camera; an elevated foot platform adapted to reduce or prevent rotational movement of a foot; a processor communicatively coupled to the depth sensing camera, the processor configured to calculate a circumference of a user's leg based on data collected from the depth sensing camera while the user has one foot positioned on the foot mat and another foot positioned on the elevated foot platform, the processor further configured to select a recommended product for a knee of the user or an ankle of the user from among a set of pre-manufactured candidate products for knees or ankles based at least in part on the circumference of the user's leg; and an output device configured to display information received from the processor, the information identifying the recommended product to the user.

2. The apparatus of claim 1, wherein the elevated foot platform comprises at least one foot well.

3. The apparatus of claim 1, wherein the foot mat is a pressure array foot mat, and wherein the processor is communicatively coupled to the pressure array foot mat and configured to receive a plurality of pressure measurements when the user is in a standing position on the pressure array foot mat.

4. The apparatus of claim 3, wherein the processor is configured to calculate an arch index of a user's foot, and to select a recommended product for the user's foot from among a set of pre-manufactured candidate products for feet based at least in part on the plurality of pressure measurements and the arch index.

5. The apparatus claim 1, wherein the processor is configured to infer the location of a leg joint of the user and to calculate the circumference of the user's leg at a target distance from the inferred location of the leg joint.

6. The apparatus claim 1, wherein the processor is configured to calculate the circumference of the user's leg while the user is in a first standing position and while the user is in a side standing position relative to the depth sensing camera, and wherein the processor is further configured to combine the calculation of the circumference of the user's lea while the user is in the first standing position and the calculation of the circumference of the user's leg while the user is in the side standing position to calculate a more accurate circumference of the leg.

7. A method of identifying a pre-manufactured candidate product for a user, the method comprising: calculating a circumference of a user's leg based on data collected from a depth sensing camera while the user has one foot positioned on a foot mat and another foot positioned on an elevated foot platform; selecting a recommended product for a knee of the user or an ankle of the user from among a set of pre-manufactured candidate products for knees or ankles based at least in part on the calculated circumference of the user's leg; and displaying the recommended product for the user on an output device.

8. The method of claim 7, further comprising receiving a plurality of pressure measurements from the foot mat when the user is in a standing position on the foot mat.

9. The method of claim 8, further comprising calculating an arch index of a user's foot and selecting a recommended product for the user's foot from among a set of pre-manufactured candidate products for feet based at least in part on the plurality of pressure measurements received from the foot mat and the calculated arch index.

10. The method of claim 7, further comprising inferring the location of a leg joint of the user and calculating the circumference of the user's leg at a target distance from the inferred leg joint.

11. The method of claim 7, further comprising calculating the circumference of the user's leg while the user is in a first standing position and while the user is in a side standing position relative to the depth sensing camera, wherein the calculations in the first standing position and the second standing position are combined to calculate a more accurate circumference of the leg.

* * * * *